(12) United States Patent
Wagner

(10) Patent No.: US 8,770,973 B2
(45) Date of Patent: Jul. 8, 2014

(54) MEDICAL HANDPIECE FOR DISPENSING FILLING MATERIAL

(75) Inventor: Hannes Wagner, Salzburg (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 856 days.

(21) Appl. No.: 12/495,034

(22) Filed: Jun. 30, 2009

(65) Prior Publication Data

US 2010/0003636 A1    Jan. 7, 2010

(30) Foreign Application Priority Data

Jul. 4, 2008 (EP) .................................... 08012081

(51) Int. Cl.
*A61C 5/04* (2006.01)

(52) U.S. Cl.
USPC .......................................................... 433/89

(58) Field of Classification Search
CPC ................................. A61C 5/062; A61C 3/00
USPC .............. 433/86, 89–90, 25, 29, 215, 41, 81, 433/118, 97, 32, 226; 604/22, 504; 606/80; 222/326, 327, 137, 145.6; 134/1, 2, 6, 134/34; 15/22.1, 97.1, 3

See application file for complete search history.

(56) References Cited

U.S. PATENT DOCUMENTS

| 8,043,088 B2 * | 10/2011 | Johnson .......................... 433/86 |
| 2006/0165832 A1 * | 7/2006 | Allan et al. ................. 425/174.2 |
| 2008/0044789 A1 * | 2/2008 | Johnson .......................... 433/81 |
| 2010/0239785 A1 * | 9/2010 | Planta Torralba et al. .... 427/600 |

FOREIGN PATENT DOCUMENTS

| DE | 10001513 A1 | 4/2001 |
| EP | 0151758 A | 8/1985 |
| EP | 1923017 A1 * | 5/2008 |
| EP | 1923018 A1 | 5/2008 |
| ES | 2323351 A1 * | 7/2009 |
| WO | WO 2006/136398 A2 | 12/2006 |

OTHER PUBLICATIONS

Search Report dated Dec. 9, 2008, from European Patent Application No. EP 08012081.9, filed Jul. 4, 2008.
International Search Report and Written Opinion from International Application No. PCT/EP2006/005973, filed Jun. 21, 2006, dated Mar. 21, 2007.

* cited by examiner

*Primary Examiner* — Cris L Rodriguez
*Assistant Examiner* — Mirayda A Aponte
(74) *Attorney, Agent, or Firm* — Klarquist Sparkman, LLP

(57) ABSTRACT

Medical handpieces for dispensing filling material are disclosed. Some handpieces comprise a connection device for a filling material container, a vibration unit for the generation and transmission of vibrations to the filling material and a conveying device for conveying filling material from the container. The vibration unit comprises a vibration exciter and a sonotrode, wherein the sonotrode and the connection device are movable relatively to each other for conveying filling material from the filling material container. In addition handpieces are described for dispensing filling material, the vibration unit of which is operable in an automated operating mode for pulsed power output on the filling material.

22 Claims, 2 Drawing Sheets

MEDICAL HANDPIECE FOR DISPENSING FILLING MATERIAL

CROSS REFERENCE TO RELATED APPLICATION

This application claims priority to and benefit of pending European Patent Application No. 08012081.9, filed Jul. 4, 2008, which is incorporated herein in its entirety by this reference.

FIELD

The present application relates to a medical device, in particular, a dental handpiece for dispensing filling material with a vibration exciter for transmitting vibrations to the filling material.

DESCRIPTION OF PRIOR ART

Such a handpiece is known, for example, from PCT patent publication WO 2006/136398, which is incorporated herein by reference. The handpiece comprises an electrically or pneumaticly driven vibration exciter, to which a sonotrode is attached. The sonotrode comprises a receptor for a filling material container and transmits the vibrations from the vibration exciter via the filling material container to the filling material. By applying the filler material with vibrations, in particular, with ultrasound vibrations, the viscosity of the material is reduced and therefore the introduction of the filling material in narrow spaces or canals, in particular, in tooth cavities or root canals is facilitated.

For conveying the filling material from the filling material container, a conveying device is provided comprising a mobile, movable piston. According to PCT patent publication WO 2006/136398, this piston is arranged within the sonotrode which is formed as a hollow swinging shaft. One disadvantage of this construction lies in the fact that the piston or other components of the conveying device touch the sonotrode and therefore influence in a disruptive manner the transmission of vibrations by the sonotrode and reduce the energy input on the filling material.

In contrast, one advantage of the present approach is therefore to provide a medical, in particular, dental handpiece for dispensing filling material on human or animal tissue or on prostheses for human or animal tissue which does not show these disadvantages and which exhibits an improved vibration transmission on the filling material.

SUMMARY

According to an embodiment, the medical handpiece for dispensing filling material on one or more of a human tissue, an animal tissue, a prosthesis for human tissue, and a prosthesis for animal tissue comprises a connection device for coupling the handpiece to a filling material container, a vibration unit for generating and transmitting vibrations to the filling material and a conveying device for conveying the filling material from the container. The vibration unit comprises a vibration exciter and a sonotrode.

In some embodiments, the sonotrode and the connection device are linearly movable towards each other and away from each other. The sonotrode can be arranged movably in the handpiece, in particular, so that it is movable through the conveying device in the direction of the connection device for the filling material container. Alternatively, the filling material container or the connection device or the connection device and the sonotrode are arranged movably in the handpiece or on the handpiece.

The sonotrode can serve both to transmit the vibrations to the filling material as well as to apply filling material from the container whereby a vibration transmission is achieved generally without disturbing influence by other components of the handpiece. In order that these two functions can be reliably carried out by a single component, i.e., the sonotrode, it can be formed substantially rigid and/or substantially straight since doing so ensures a particularly effective vibration transmission with low losses or damping effects and thereby a sufficiently great energy input on the filling material, in particular, on highly viscous synthetic resin-based filling materials and a continuous conveyance of the filling material from the container. The rigid form of the sonotrode effects a noticeably improved vibration transmission, particularly with vibration exciters which generate a spatial, for example, radial and axial vibration.

Different kinds of filling materials can be dispensed with the medical, in particular, dental handpiece with which a change in viscosity is achieved by applying sound or ultrasound which facilitates the filling of the filling material into a cavity, for example, cements or synthetic resin-based filling materials. Preferably, the handpiece is used for dispensing synthetic resin-based dental filling materials which polymerize through the effect of light or harden (so-called composites), in particular, highly viscous synthetic resin-based dental filling materials having a high share of inorganic fillers.

The dispensing of filling materials takes place preferably directly on or in human or animal tissue in order to fill therewith hollow spaces, cavities, for example caused by caries or prepared cavities, or canals, for example, root canals. Alternatively, the filling materials are used to secure prostheses, for example, dental inlays, on human or animal tissue, wherein hereby the filling material in turn is dispensed on the tissue and or also on the prostheses.

The connection device for the filling material container is formed as a hollow space, recess or coupling element, wherein at least a part of the container is directly attachable in or on it. Alternatively, a support or carrying element for the filling material container can be attached to the connection device. The connection device is formed as a part of the handpiece, in particular, as a part of the outer sleeve of the handpiece.

The vibration exciter of the vibration unit, specifically, the sound transducer as a part of the vibration exciter, can be formed as pneumatic or as electrically operated vibrator, in particular, as piezo vibrator or as magnetostrictive vibrator.

According to an embodiment, the connection device for the filling material container and the sonotrode comprise a common, straight center axis so that by moving the sonotrode along the center axis, the sonotrode can penetrate into the connection device. By this construction along the common center axis, the energy input on the filling material is further improved since the vibration transmission is carried out exclusively via components arranged straight behind each other. In addition, the handpiece or a part thereof in the case of a handpiece formed, for example, in the shape of a pistol in which the connection device and the sonotrode are arranged, is formed substantially straight. Also advantageous is when the longitudinal axis of this section or of the complete handpiece and the center axes of the connection device and the sonotrode coincide so that the connection device and the sonotrode are arranged centrically in this section or in the handpiece. In order to facilitate the dispensing of the filling material for the user, the filling material container is, in particular, according to this embodiment formed curved or angled, whereby at least a portion of the filling material container is angularly arranged to a common straight center axis of the connection device and the sonotrode or to the longitudinal axis of the handpiece or of the above-mentioned handpiece section.

By providing a single bearing place for the vibration unit, the vibration transmission is additionally improved. Preferably, the vibration unit comprises an electrically or pneumatically operable sound transducer, a counterweight and the sonotrode, in which the only bearing place is provided in the area of the sound transducer and comprises a sealing compound surrounding the sound transducer. The sealing compound can comprise, for example, a synthetic resin, particularly a silicone resin. The use of a sealing compound as bearing material has the additional advantage that the electrical components of the handpiece are protected from contaminants and moisture penetrating into the handpiece.

Preferably, the sonotrode is firmly connected to the other components of the vibration unit so that the entire vibration unit is formed to be moveable for conveying the filling material out of its container. To be able to move the vibration unit inside the handpiece with little effort, the vibration unit is accommodated in a sliding sleeve which is arranged slidably in the handpiece, wherein at least that part of the sonotrode which follows or which penetrates into the connection device for the filling material container, projects from the slide sleeve.

According to another embodiment, an anti-rotation lock is provided in the handpiece which prevents a twisting of the vibration unit or the sonotrode relative to the handpiece. The anti-rotation lock serves for straight guidance of the sonotrode in the direction of the connection device or away from the latter without having any twisting occurring through which, for example, the electrical or pneumatic leads for driving the vibration exciter twist, interrupt, break or become damaged. The anti-rotation lock also prevents a twisting of the vibration unit or of the sonotrode when during the use a torque has an effect on the sonotrode, for example, during the insertion of a filling material container into the connection device or during the release of the front end of the sonotrode of the handpiece.

Since the sonotrode contacts the non-sterile filling material container or perhaps comes into contact with filling material or tissue particles or body fluids of the patient, it is advisable to form the sonotrode such that it can be cleaned in a simple manner by the user. Preferably, this is achieved by constructing the sonotrode as two parts, wherein that part of the sonotrode which is further away from the vibration exciter is detachable from the rest of the sonotrode and removable in a simple manner from the handpiece. Preferably, this sonotrode part is taken out of the handpiece through the connection device and subsequently can be cleaned or sterilized without difficulty.

According to an another aspect, the vibration unit of the medical or dental handpiece for dispensing filling material on human or animal tissue or on prostheses for human or animal tissue can be operated in an automated operating mode for pulsed power output on the filling material. This embodiment is based on the observation that through the applying the filling material with vibrations, in particular, with ultrasound vibrations, the filling material is strongly heated, for example, through friction of the sonotrode at the filling material container, through friction of the filling material at the container case and through friction of filling material particles on each other. The heating can thereby be so strong that by the application of the filling material on living tissue, the patient has a sensation of pain. In addition, through the warming of the filling material the danger of shrinkage increases during hardening of the filling material.

By the operation of the handpiece in the automated operating mode for pulsed power output on the filling material these disadvantages are overcome and particularly the warming of the filling material reduces without having the delivery of the viscous filling material from the filling materials container or the course of the filling procedure be impaired. The pulse rate of the automated operating mode for pulsed power output should amount to at least 10 Hz, preferably more than 50 Hz, particularly preferred for this is between 90-100 Hz.

During the operation of the handpiece in the automated operating mode for pulsed power output, the filling material is applied with at least two different vibration powers or the vibration unit switches alternating between at least two different vibration powers applied. One of the two vibration powers also can be 0 watts according to an embodiment so that that no energy input therefore takes place on the filling material. Alternatively, both vibration powers during the automated operation for the pulsed power output are greater than 0 watts, for example, the power output can amount alternating in approximately 5 watts and in approximately 0.5 watts or in approximately 10 watts and in approximately 1 watt.

It was also observed that through the automated, pulsed operation of the handpiece or the pulsed power output, the modelling of the filling material already dispensed on the preparation site is possible or is improved since through the pulsed operation the nozzle or the front end of the filling material container through which the filling material is dispensed and which is simultaneously also used for modelling, or a separate modelling tool which can be connected to the handpiece are put into vibration more strongly through the sonotrode or execute greater vibration amplitudes than by a continuous vibration transmission or power output.

According to an embodiment, the vibration unit for the pulsed power output can be switched, alternating between a first condition in which it applies vibrations, and a second condition in which it does not apply any vibrations. The switching between the two conditions occurs preferably by a circuit of a control and/or regulating device with a microcontroller. Especially preferred are the control and/or regulating device switches the vibration unit alternating on and off, for example, by applying pulsed control or drive signals. In particular, it switches, alternating on and off, the supply of the drive medium for the vibration exciter, therefore, the power supply for an electrically operable vibration exciter or the compressed gas supply for a pneumatically operable vibration exciter. The control and/or regulating device is arranged either entirely in the handpiece or in a basic unit connected to the handpiece via a cable or partly in the handpiece and in the basic unit.

Alternatively, the vibration unit, in particular, the vibration exciter for the pulsed power output is operable alternately with two different frequencies. One of the two frequencies is thereby selected such that it is equal to a resonance frequency of the sonotrode so that the sonotrode is set into vibration and consequently transmits a first high vibration on the filling material and the filling material container. The other one of the two frequencies does not correspond to any resonance frequency of the sonotrode so that the latter does not transmit any vibrations or is at least only insignificantly set into vibration, whereby none or only a low vibration power is transmitted on the filling material and the filling material container.

The change between the at least two different frequencies is effected in turn by a control circuit or a circuit of a control and/or regulating device with a micro-controller, in particular through the supply of different control or drive signals to the vibration exciter, for example, through the variation of the frequency of the control voltage applied to the piezo vibration or magnetostrictive vibration.

According to yet another embodiment, the vibration unit is operable in a two-phase drive mode, in which the first drive phase comprises a substantially constant power output on the filling material and the second phase following subsequently, the automated mode for pulsed power output. Thereby is achieved that with the start of a treatment or after a treatment pause, a first portion filling material is dispensed without delay. The first continuous driving phase lasts approximately between two and 15 seconds, preferably between four and ten seconds, especially preferred in approximately five seconds. The preferred automated process of the two-phase drive mode, in particular the duration of the first drive phase and the pulsed power output is again monitored by a control and/or regulating device.

The pulsed power output on the filling material of course can also be realized via other measures. For example, the sonotrode can be designed bipartite (i.e., as a two-piece assembly), wherein the two parts are alternating coupled together and decoupled from each other, for example, by means of a magnetic coupling to carry out or interrupt the sound transmission on the filling material. Accordingly, the sonotrode and the vibration exciter can also be formed to alternating couple together and to decouple from each other.

According to another embodiment, the handpiece or the basic unit comprises an actuating element for selecting the pulse duration of the automated operating mode for pulsed power output or for selecting the pulse rate of the automated operating mode for the pulsed power output or for determining the duration of the first drive phase or for selecting the power transmittable to the filling material.

A method for dispensing filling material, in particular, a synthetic resin-based dental filling material on human or animal tissue with a handpiece described in the preceding comprising the step that the sonotrode through the conveying device is moved in the direction of the connection device for the filling material container. The sonotrode pushes thereby filling material from the filling material container. The displacement of the sonotrode or of the entire vibration unit connected with the sonotrode and therewith the expelling of the filling material from the container can take place either simultaneously with the vibration transmission through the sonotrode but also without the setting in vibration of the sonotrode as well.

Another method of dispensing filling material, in particular, synthetic resin-based dental filling material on a human or animal tissue with a handpiece described herein comprises operating the vibration unit in an automated operating mode in which a pulsed power output is carried out on the filling material. In such methods, the vibrations applied to the filling material can alternate between being applied and not being applied by the vibration unit.

A method for the modelling of filling material dispensed with a handpiece described in the preceding on a preparation site comprises operating the vibration unit in an automated operating mode in which a pulsed power output is carried out on the filling material. The pulsed power output is applied, for example, via the container of the filling material, in particular, via its dispensing end for the filling material, which is often formed as a nozzle or via the connection device for the filling material container or via a support or carrying element secured therein for the filling material container or via a modelling tool on the filling material. Alternating vibrations can be applied or not applied by the vibration unit, the vibrations being transmitted to the filling material located on the preparation site so that the viscosity of the filling material is reduced and the formability of the filling material improved. The modelling tool can be formed, for example, as a spatula or a rod and can be detachably connected with the connection device, so that vibrations can be transmitted thereto.

These, and other embodiments, will be explained in the following on the basis of preferred embodiments with reference to the enclosed drawings:

DETAILED DESCRIPTION

Figure 1:
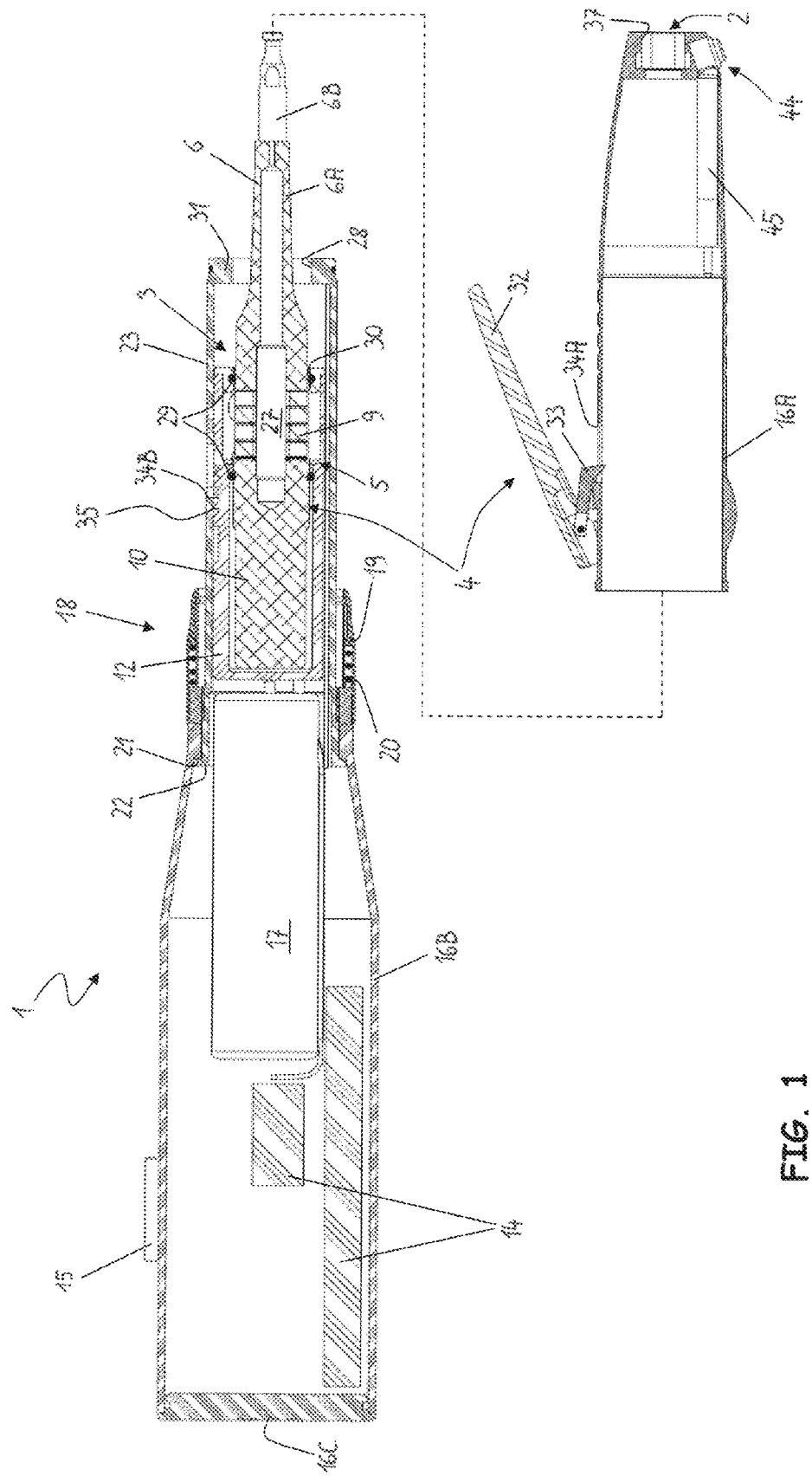
FIG. 1 shows a cross-sectional view of a first embodiment of a medical, in particular, dental handpiece for dispensing filling material with parts of the handpiece shown separated.
Figures 2, 3:
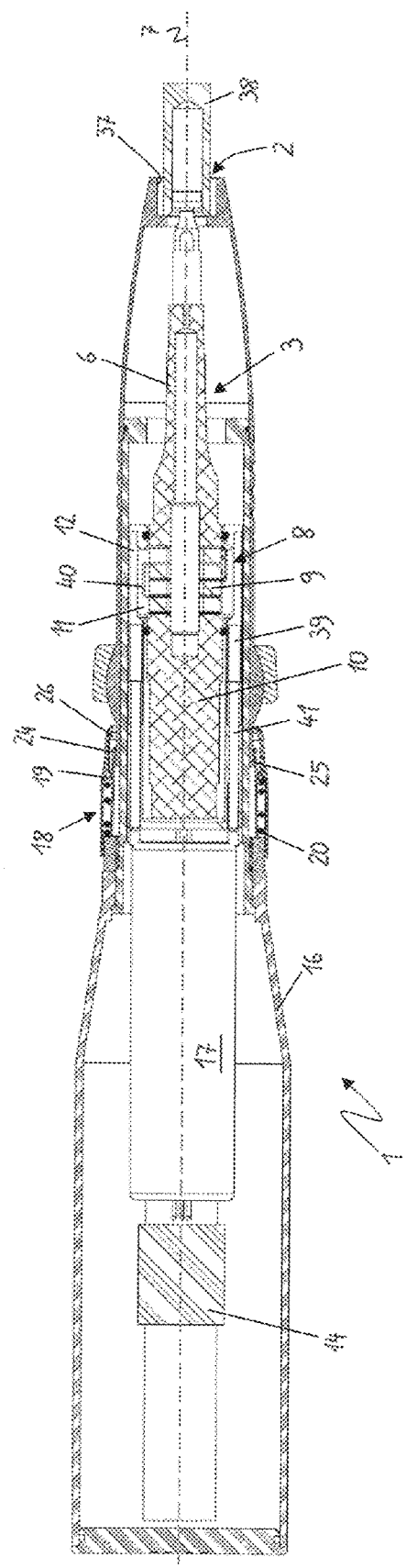
FIG. 2 shows a further cross-sectional view of the handpiece from FIG. 1 along a second cutting plane with the parts of the handpiece joined together.
FIG. 3 shows a cross-sectional view of a second embodiment of a handpiece for dispensing a filling material with an alternatively formed conveying device.

As shown in FIGS. 1 to 3 a medical, in particular, a dental handpiece 1, 1A for dispensing filling material on human or animal tissue or on prostheses for human or animal tissue, is formed as a cordless, battery-operated hand element or handpiece. The handpiece can also be operated by means of an external current source, in which it has an electrical lead to the external current source. In this case, it is also possible that the handpiece for dispensing a filling material comprises a base station or a basic unit with which it is connected via a power cable, which preferably includes at least the electrical lead and, as the case may be, also further media lines. Furthermore, on the basic unit there are preferably provided control or actuating elements for adjusting operating parameters or for selecting operating programs or a display for an operating parameter.

The handpiece 1, 1A comprises an outer sleeve 16 which is in one piece or constructed in several parts, as shown in the FIGS. 1-3. The outer sleeve 16, specifically, the entire handpiece 1, 1A, is separable into two parts, wherein the front or first handpiece part comprises the outer sleeve part 16A, the connection device 2 and a portion of the conveying device 4. The outer sleeve part 16A comes into contact with the patient during the treatment. Through the separability, the outer sleeve part 16A can be detached from the remaining handpiece 1, 1A and cleaned, disinfected or sterilized, to prevent the transmission of germs between patients. A lid 16C detachably connected to the outer sleeve 16B closes the handpiece 1, 1A at one end.

The rear or second handpiece part comprises the outer sleeve part 16B, preferably with the power supply for the handpiece 1, 1A, for example, with a battery or an accumulator 17, a control and/or regulating device 14 connected with the power supply and at least part of the vibration unit 3, in particular, with the vibration exciter 5. The power supply and at least part of the vibration unit 3 are housed in a protective sleeve 23. For the connection of the protective sleeve 23 with the outer sleeve 16B, these are at least in one section pushed into each other in a contacting manner. The two sleeves 16B and 23 support each other through a shoulder 21 and a projection 22 in each case at one of the two sleeves 16B, 23, wherein they are additionally or alternatively screwed together.

The locking of the two handpiece- or outer sleeve parts 16A, 16B occurs via a releasable locking device 18. The locking device 18 comprises a locking sleeve 19 moveably, for example, slidably attached to the handpiece 1, 1A, which is prestressed in its locking position by a spring element 20. At least one resiliently formed clamping strap 24 is provided between the locking sleeve 19 and the protective sleeve 23, which comprises at its free end facing the connection device 2 a detent nose pointing radially inwardly in the direction of the center axis 7. In the locked condition as it is represented in FIG. 2, the locking sleeve 19 presses with its inner side the clamping strap 24 radially inwards (in the direction of the center axis 7) so that the detent nose engages behind a counter element 25 for example, a projection, arranged at the outer side of the outer sleeve part 16A, whereby an axial release of both outer sleeve parts 16A, 16B is prevented. The outer sleeve part 16A is pushed on the protective sleeve 23 in this locked condition and clamped additionally between the latter and the locking sleeve 19, respectively, the clamp strip 24.

To release the two handpiece- or outer sleeve parts 16A, 16B the locking sleeve 19 is pulled against the force of the spring element 20 in the direction of the accumulator 17, whereby the clamping strap 24 and the detent nose, which are stationary relative to the locking sleeve 19 can turn aside radially outwards, away from the center axis 7, in an annular groove 26 and release the counter element 25 so that the outer sleeve part 16A can be pulled out of the locking sleeve 19 and pulled down from the protective sleeve 23.

The vibration unit 3 of the handpiece 1 comprises a vibration exciter 5 with a sound transducer 9 and a metallic counterweight 10 and a vibration transmitter, such as a sonotrode 6. The sound transducer 9, the metallic counterweight 10 and the sonotrode 6 are arranged on a common support element, for example, a pin 27. The pin 27 has a connection device at each of its two ends, preferably a thread to which the sonotrode 6 and the counterweight 10 are fastened. Between the two connection devices, the pin 27 has a smooth surface on which are arranged an intermediate layer or an insulation sleeve and over that the vibration exciter 5.

The vibration exciter 5 comprises several, for example, four or five piezo elements which are tensioned between the counterweight 10 and the sonotrode 6. When the piezo elements are set under electrical voltage, they start to vibrate in the known way, particularly in the ultrasound area and transmit their vibrations onto the sonotrode 6.

The sonotrode 6 comprises an oblong, hollow shaft which is formed substantially rigid and substantially or completely straight. The sonotrode is preferably made of metal, and preferably made of titanium or another suitable metal or alloy. It projects through an opening 28 in the protective sleeve 23 up to the outer sleeve part 16A or beyond the latter. The sonotrode 6 consists of two parts 6A, 6B, which are connected with each other in a detachable manner, for example, by a screw thread or by a bayonet connection. The part 6B of the sonotrode 6 which is further removed from the vibration exciter 5 can therefore be detached in an advantageous manner from the second handpiece part 16B and the part 6A of the sonotrode 6 connected therewith and be cleaned.

The vibration unit 3 is supported at a single bearing place 8 in the handpiece 1 which is located in the region of the sound transducer 9. The support contains a sealing compound 11, for example, silicone resin with which the sound transducer 9 is molded-in. In an advantageous manner, the sealing compound 11 also serves for the protection and for the electrical insulation of the vibration exciter 5. Two O rings 29, which are arranged on the counterweight 10 and on the sonotrode 6, respectively, near the sound transducer 9, center the vibration unit 3 in the handpiece 1 and serve as sealing elements also when pouring the sealing compound 11.

The vibration unit 3 is housed in a sliding sleeve 12 and supported by the bearing place 8 therein. The sliding sleeve 12 consists preferably of synthetic material and has one side an opening 30 through which a part of the vibration unit 3 projects, in particular, at least a part of the sonotrode 6. The sonotrode 6 and the counterweight 10 are separated by a gap from the inside wall of the sliding sleeve 12 and therefore do not touch the sliding sleeve 12 for the purpose of undisturbed vibration. The sliding sleeve 12 and the vibration unit 3 held therein are formed to be movable relative to the protective sleeve 23, respectively, to the outer sleeve 16. The sliding sleeve 12 slides along the inside wall of the protective sleeve 23, wherein its movement is limited by a stop which, for example, is formed by an end wall 31 of the protective sleeve 23.

The conveying device 4 of the handpiece 1 comprises, among other things, a lever 32 which is fastened to the outside of the handpiece 1 and manually operable, e.g., by shifting or pivoting by a user. The lever 32 is connected to a driver device which includes a catch 33. The catch 33 projects with its wedge-shaped end through an opening 34A of the outer sleeve 16 and through an opening 34B of the protective sleeve 23 into the interior of the protective sleeve 23 and engages a row of teeth 35 arranged on the outside of the sliding sleeve 12. The catch 33 is prestressed by a spring, not illustrated, in the direction of the row of teeth 35. By pivoting the lever 32 alternating in the direction of the openings 34A, 34B and in the opposite direction, the sliding sleeve 12 and the sonotrode 6 are moved in the direction of the connection device 2. This happens in that the wedge-shaped front end of the catch 33 engages between two teeth of the row of teeth 35 and moves it when the lever 32 is turned in the direction of the openings 34A, 34B. When the lever 32 is pivoted in the opposite direction, the wedge-shaped front end of the catch 33 releases itself from the two teeth of the row of teeth 35 in order to engage again by the next movement of the lever 32 in the direction of the openings 34A, 34B the row of teeth 35.

According to an alternative embodiment, a motorized conveyor device is provided in which instead of the lever 32, an electrical drive motor or a pneumatic drive comprising, in particular, a piston movable by means of compressed gas moves the sonotrode 6.

The conveying device 4' according to FIG. 3 comprises likewise a manually operable, pivotal or rotational lever 32' as well as a gear rack 36 which is connected to the sliding sleeve 12. A catch 33' with a wedge-shaped front end is provided in turn at the lever 32'. The catch 33' is prestressed by a spring in the direction of the gear rack 36. The gear rack 36, the sliding sleeve 12 and the sonotrode 6 are moved in the direction of the connection device 2 through the pivoting of the lever 32' alternating to the handpiece 1A and in the opposite direction. This happens as described above already for the row of teeth 35 at the sliding sleeve 12, through alternating engagement and release of the catch 33' in the teeth of gear rack 36. Compared to the conveying device 4 according to FIG. 1, the rotating axis around which the lever 32' turns, as well as the entire carrier device including the catch 33' are arranged inside the handpiece 1A.

At the distal end of the handpiece 1, a connection device 2 is provided for a filling material container 46. For conveying the filling material from the filling material container, a conveying device is provided comprising a mobile, movable piston 47. The connection device 2 is positioned adjacent to the sonotrode 6 and/or is formed as a part of the sonotrode 6 and therefore transmits vibrations to the filling material. The connection device 2 in accordance with FIG. 1 comprises a recess 37 which is part of the outer sleeve 16. In the recess 37, at least a part of the filling material container 46 can be inserted and fastened therein via a fastening device, for example, a screw thread or a bayonet coupling. A support or carrier element 38 for the filling material container 46 which is fastened to the recess 37 supports and rests the filling material container.

As already described, the vibration unit 3, in particular, the sonotrode 6 is formed to be movable in respect of the remaining handpiece 1 and thus also of the connection device 2 and a filling material container 46 held therein. As can be recognized particularly from FIG. 2, by actuating the lever 32, 32' the sonotrode 6 is moved in the direction of the connection device 2 or penetrates into the latter and in the filling material container 46, whereby filling material is driven out of the filling material container and dispensed on the preparation site. The vibration unit 3, and particularly the sonotrode 6, serve not only for the transmission of vibrations onto the filling material to reduce its viscosity, but they are thereby also part of the conveying device 4, 4' for dispensing the filling material from the filling material container.

The connection device 2 and the sonotrode 6 have a common, straight center axis 7, along which the sonotrode 6 is movable, in order to preferably penetrate into the connection device 2. This center axis 7 is also preferably the straight center axis of the handpiece 1 so that the sonotrode 6 and the connection device 2 are arranged centrically at the handpiece 1 (see FIG. 2).

The power supply of the vibration unit 3 for the drive of the sound transducer 9 occurs by an external power source or by a power source provided in the handpiece 1, 1A, for example, the battery or accumulator 17. A compressed gas source serves as the power source in the case of a pneumatic sound transducer. In the case of an electrically powered sound transducer, a current source serves as the power source. Regardless of the type of power source, the supply of power to the sound transducer 9 has to be formed such that also during the displacement of the vibration unit 3 for conveying the filling material from the filling material container 46 or regardless of the position which the vibration unit 3 assumes in the handpiece 1, 1A, a reliable power supply of the vibration unit 3, in particular, of the sound transducer 9 is ensured. This is achieved because at least one part of the power supply is connected with the vibration unit 3, in particular, the vibration exciter 5, and is moveable with the latter relative to the remaining handpiece 1, 1A or to the outer sleeve 16.

With a pneumatic sound transducer, the power supply unit, for example, comprises a tube which conducts the compressed gas to the sound transducer, wherein an end of the tube is connected to the sound transducer and follows the displacement movement of the sound transducer or of the complete vibration unit. The tube is formed flexibly to compensate for the length of the path covered during the displacement by the sound transducer. Thus, the tube can be wound spirally, for example, or it can comprise a flexible material or it can comprise two tube parts telescopically connected to each other and are relatively movable to each other.

With an electrically operated sound transducer, the power supply unit comprises electrical contacts or leads which are connected to the sound transducer and follow the displacement movement of the sound transducer or the entire vibration unit. The electrical contacts or leads include, for example, spirally-wound leads, spring-, sliding-, rolling-contacts or contacts built up in a two-piece configuration which are movable in each other. According to FIG. 2, two sleeve-like, electrically conductive, metallic contacts 39 are provided, which are connected to the sliding sleeve 12 and with the latter and the vibration unit 3 are moved relative to the remaining handpiece 1, 1A. The contacts 39, in particular, are inserted in the wall of the sliding sleeve 12. The sleeve-shaped contacts 39 are connected with the disc-shaped piezo elements of the sound transducer 9 via likewise movable wires or leads 40. The sleeve-shaped contacts 39 accommodate spiral springs (not shown) as well as electrically conducive contact pins 41. The contact pins 41 are connected with the power source, for example, the battery or accumulator 17 and slidaby arranged in the sleeve-shaped contacts 39, thereby ensuring a reliable power supply of the sound transducer 9 independently of its position via the contact pins 41, the sleeve-shaped contacts 39 with the spiral springs and the wires 40.

According to another embodiment, it is also possible to arrange the accumulator 17 movably in the handpiece 1, 1A so that the accumulator 17 also follows the sliding movement of the vibration unit. For example, a recess for this can be provided for the accumulator 17 at the sliding sleeve 12.

In the handpiece 1A of the FIG. 3 an anti-rotation lock 13 can be recognized, which prevents a rotation of the vibration unit 3 or of the sonotrode 6 relative to the handpiece 1, 1A. The anti-rotation lock 13 serves in particular for the straight guidance of the sonotrode 6 in the direction of the connection device 2 or away from it without causing any twisting. The anti-rotation lock 13 comprises a locking element 42 arranged in a rotationally-fixed manner relative to the handpiece 1A, for example, a pin or a ball, engaging a recess, a groove or a bore 43 of the sliding sleeve 12 and therewith preventing a rotational movement of the vibration unit 3 and the sliding sleeve 12 around their own axes.

According to a preferred embodiment, the handpiece 1 is equipped in addition with a lighting device 44, which provides radiation with a wavelength and radiant power for the hardening of filling material. The lighting device 44 comprises preferably one or a plurality of light-emitting diodes which are arranged in a hermetically encapsulated lighting module in order to withstand repeated sterilizing. The lighting device 44 is arranged at the distal end of the handpiece 1, preferably in the vicinity of the connection device 2 so that it can emit its radiation directly on the filling material, i.e. without use of a separate light guide.

The lighting device 44 is electrically connected via contacts and leads 45 to a power source, for example, the accumulator 17. It is also connected to the control and/or regulating device 14 which monitors, e.g., processes, the power supply for the light-emitting diodes and monitors, adjusts or specifies the operating parameters of the lighting device 44. The control and/or regulating device 14, in particular, comprises a switching unit which is configured such that optionally vibrations from the vibration unit 3 are applied on the filling material in the filling material container 46 or the lighting device 44 emits radiation in the direction of the preparation site.

The control and/or regulating device 14 is also connected with the vibration unit 3 to control and to regulate its operation, as this has been already described in detail above. The control and/or regulating device 14 operates the vibration unit, in particular, in an automated operating mode for pulsed power output on the filling material during which the filling material is applied with at least two different vibration powers. A too strong warming of the filling material is prevented by this operating mode. The frequency of the automated operating mode for pulsed power output amounts to at least 10 Hz, preferably more than 50 Hz, especially preferably is between approximately 90-200 Hz.

Preferably, the control and/or regulating device 14 switches the vibration unit 3 alternately between a first condition in which it applies vibrations, and a second condition in which it does not apply any vibrations. In a preferred embodiment, the control and/or regulating device 14 switches the vibration unit 3 alternately on and off, in particular, by switching the power supply from the power source to the vibration unit 3 on and off. For this purpose the control and/or regulating device 14 is also connected to the power source, in particular, to the accumulator 17.

The control and/or regulating device 14 operates the vibration unit 3 also in the two-phase drive mode, wherein the first drive phase comprises a substantially constant power output on the filling material and the second subsequently following phase, comprises the automated mode for pulsed power output.

At least one control- or actuating element 15 is provided on the handpiece 1 which is connected to the control and/or regulating device 14. With the at least one actuating element 15, the user can set, select or adjust the operating parameters for the lighting device 44 and/or for the operation of the vibration unit 3, in particular, for its operation in the automated operating mode for pulsed power output or switch on and off the lighting device 44 or the vibration unit 3. The control or actuating element 15 comprises, inter alia, an operating device at the outer sleeve 16 which is simple to operate for the user, for example a push button or a knob.

The use of the handpiece 1, 1A was already described above in a method for modelling of already dispensed filling material on a preparation site, in which the vibration unit 3 is operated in an automated operating mode by which a pulsed power output on the filling material or on the container of the filling material, in particular, on its dispensing end for the filling material, or on a modelling tool is carried out. It was observed that the effect of the modelling method clearly increased with pulse rates over 500 Hz, preferably at pulse rates over 1,000 Hz. According to a preferred embodiment, the control and/or regulating device 14 comprises therefore at least two operating programs for the operation of the vibration unit 3. The first operating program to avoid a too strong warming of the filling material operates the vibration unit 3 in an automated operating mode for pulsed power output with a first, low pulse rate or frequency, for example, in approximately 100 Hz at maximum. The second operating program for the modelling of filling material dispensed on a preparation site operates the vibration unit 3 in an automated operating mode for the pulsed power output with a second, high pulse rate or frequency of, for example, at least approximately 500 Hz, preferably at least approximately 1,000 Hz. A control- or setting element 15 on the handpiece 1, 1A is provided for selecting one of the two operating programs.

The scope of the following claims is not limited to the embodiments described but includes all designs which use or contain the principles and analogous functional principles of this disclosure. Each of the features of each described embodiment can also be combined with one another.

What is claimed is:

1. A medical handpiece for dispensing filling material on one or more of a human tissue, an animal tissue, a prosthesis for human tissue, and a prosthesis for animal tissue, the handpiece comprising:
a connection device for coupling the handpiece to a filling material container, a vibration unit for generating and transmitting vibrations to the filling material and a conveying device for conveying the filling material from the container, wherein the vibration unit comprises a vibration exciter and a sonotrode coupled to the vibration exciter, and wherein the sonotrode and the connection device are movable relative to each other for conveying the filling material from the filling material container in a first mode of movement by which the sonotrode transmits vibrations generated by the vibration exciter onto the filling material substantially without any net displacement and in a second mode of movement by which the sonotrode is displaced towards the connection device to push the filling material from the filling material container.

2. The medical handpiece according to claim 1, wherein the medical handpiece comprises a dental handpiece.

3. The medical handpiece according to claim 1, wherein the sonotrode is movable by the conveying device in the direction of the connection device for the filling material container.

4. The medical handpiece according to claim 3, wherein the conveying device comprises one of a lever device, an electrical drive motor, a pneumatic drive or a piston movable by compressed gas to move the sonotrode.

5. The medical handpiece according to claim 1, wherein the connection device for the filling material container and the sonotrode comprises a common, straight central axis along which the sonotrode is movable.

6. The medical handpiece according to claim 1, wherein the vibration unit comprises a single bearing portion and wherein the vibration exciter comprises a sound transducer and a counterweight, and wherein the single bearing portion is positioned adjacent the sound transducer and comprises a sealing compound surrounding the sound transducer.

7. The medical handpiece according to claim 1, comprising a power supply unit for supplying the vibration exciter with drive energy, wherein at least a part of the power supply unit is connected with the vibration exciter and is movable therewith.

8. The medical handpiece according to claim 1, wherein the vibration unit is housed in a sliding sleeve, which is slidably arranged in the handpiece, wherein at least a part of the sonotrode projects out of the sliding sleeve.

9. The medical handpiece according to claim 1, comprising an anti-rotation lock fixing the vibration unit.

10. The medical handpiece according to claim 1, wherein the sonotrode comprises two parts separable from each other.

11. The medical handpiece according to claim 1, wherein the sonotrode comprises a shaft which is at least one of: oblong, hollow, substantially rigid, substantially or completely straight.

12. The medical handpiece of claim 1, wherein the connection device is configured such that the first mode of movement and the second mode of movement of the sonotrode occur simultaneously.

13. A medical handpiece for dispensing filling material on one or more of a human tissue, an animal tissue, a prosthesis for human tissue, and a prosthesis for animal tissue, the handpiece comprising:
a connection device for a filling material container, a vibration unit for the generation and transmission of vibrations on the filling material and a conveying device for conveying the filling material from the container, wherein the vibration unit is operable in an automated operating mode for pulsed power output on the filling material, wherein for providing the pulsed power output, the vibration unit is configured to be one of:
i) switched alternatingly between a first condition in which the vibration unit applies vibrations to the filling material, and a second condition in which the vibration unit does not apply any vibrations to the filling material, or ii) operated alternatingly with two different frequencies.

14. The medical handpiece according to claim 13, wherein the vibration unit is operable in a two-phased drive mode, wherein the first operating phase comprises a substantially constant power output on the filling material and the second phase following subsequently comprises the automated operating mode for pulsed power output.

15. The medical handpiece according to claim 13, wherein the pulse rate of the automated operating mode for pulsed power output is at least 10 Hz.

16. The medical handpiece according to claim 13, comprising
a control and/or regulating device for controlling and/or regulating the automated operating mode for pulsed power output, wherein the control and/or regulating device comprises at least one actuating element for selecting the pulse duration of the automated operating mode for pulsed power output or for selecting the pulse rate of the automated operating mode for pulsed power output or for fixing the duration of the first drive phase or for selecting the power transmittable on the filling material.

17. The medical handpiece according to claim 13, wherein the pulse rate of the automated operating mode for pulsed power output is at least 50 Hz.

18. The medical handpiece according to claim 13, wherein the vibration unit is configured to be alternatingly switched on and off in order to alternatingly switch between the first condition in which the vibration unit applies vibrations to the filling material, and the second condition in which the vibration unit does not apply any vibrations to the filling material.

19. A method for dispensing filling material on one or more of a human tissue, an animal tissue, a prosthesis for human tissue, and a prosthesis for animal tissue with a handpiece comprising a connection device for coupling the handpiece to a filling material container, a vibration unit comprising a sonotrode for generating and transmitting vibrations to the filling material and a conveying device for conveying the filling material from the container, the method comprising:
moving the sonotrode with the conveying device towards the connection device for the filling material container, such that the sonotrode pushes filling material from the filling material container.

20. A method for use in one or both of dispensing filling material on one or more of a human tissue, an animal tissue, a prosthesis for human tissue, and a prosthesis for animal tissue, and modelling of filling material dispensed on a preparation site with a handpiece comprising a connection device for a filling material container, a vibration unit for the generation and transmission of vibrations on the filling material and a conveying device for conveying the filling material from the container, the method comprising:
operating the vibration unit in an automated operating mode in which a pulsed power output is transmitted on the filling material, wherein operating the vibration unit comprises one of:

i) alternatingly switching the vibration unit between a first condition in which the vibration unit applies vibrations to the filling material, and a second condition in which the vibration unit does not apply any vibrations to the filling material, or ii) alternatingly operating the vibration unit with two different frequencies.

21. The method according to claim 20, wherein the vibration unit is operated in a two-phase drive mode, wherein the first operating phase comprises a substantially constant power output applied to the filling material, and the second phase comprises the automated operating mode for pulsed power output, wherein the second phase is subsequent to the first phase.

22. The method according to claim 20, wherein alternatingly switching the vibration unit between a first condition in which the vibration unit applies vibrations to the filling material, and a second condition in which the vibration unit does not apply any vibrations to the filling material comprises alternatingly switching the vibration unit on and off.

* * * * *